(12) United States Patent
Zhang et al.

(10) Patent No.: US 12,721,648 B2
(45) Date of Patent: Sep. 1, 2026

(54) SURGICAL IMPLEMENT FOR PIERCING TISSUE

(71) Applicant: Ningbo No. 1 Hospital, Ningbo (CN)

(72) Inventors: Moucheng Zhang, Ningbo (CN); Yafang Hu, Ningbo (CN); Kaijun Gao, Ningbo (CN); Liangqi Guo, Ningbo (CN); Jiyun Zhu, Ningbo (CN); Zhilong Yan, Ningbo (CN); Zhiping Zhang, Ningbo (CN); Jianming Xie, Ningbo (CN); Yongfang Yin, Ningbo (CN); Bin Yang, Ningbo (CN)

(73) Assignee: Ningbo No. 1 Hospital, Ningbo (CN)

( * ) Notice: Subject to any disclaimer, the term of this patent is extended or adjusted under 35 U.S.C. 154(b) by 1244 days.

(21) Appl. No.: 17/650,148

(22) Filed: Feb. 7, 2022

(65) Prior Publication Data

US 2023/0248387 A1 Aug. 10, 2023

(51) Int. Cl.
*A61B 17/34* (2006.01)
*A61B 1/313* (2006.01)
*A61B 17/00* (2006.01)

(52) U.S. Cl.
CPC ........ *A61B 17/3417* (2013.01); *A61B 1/3132* (2013.01); *A61B 17/00234* (2013.01); *A61B 2017/00336* (2013.01); *A61B 2017/00371* (2013.01)

(58) Field of Classification Search
CPC .......... A61M 25/04; A61M 2025/0233; A61M 2025/024; A61M 2025/028; A61M 2025/0293; A61B 17/34; A61B 17/3417; A61B 17/00234; A61B 17/3439; A61B 2017/00336; A61B 2017/00371; A61B 2017/3484; A61B 2017/3486; A61B 2017/3488; A61B 2017/3492; A61B 1/3132; Y10T 29/4993; Y10T 29/4994; F16J 15/028; F16J 15/127
See application file for complete search history.

(56) References Cited

U.S. PATENT DOCUMENTS

| | | | | |
|---|---|---|---|---|
| 3,039,468 A * | 6/1962 | Price | A61D 1/14 | 604/107 |
| 5,445,615 A * | 8/1995 | Yoon | A61B 17/3423 | 604/99.04 |
| 5,888,196 A * | 3/1999 | Bonutti | A61B 17/0218 | 606/198 |
| 2005/0119685 A1* | 6/2005 | Smith | A61B 17/3439 | 606/198 |

(Continued)

*Primary Examiner* — Michael J Tsai
*Assistant Examiner* — Justin L Zamory
(74) *Attorney, Agent, or Firm* — Wang Law Firm, Inc.

(57) ABSTRACT

A surgical tool for piercing tissue of a body comprises a hollow external component (1) having a peripheral wall (11), an internal component (2) movable disposed inside the external component (1) and having a piercing head (21); when the piercing head (21) and the internal component (2) retract relative to the external component (1), the movable component (3) deforms partially, expands outwardly in a radial direction, and fills the bladder (6). The movable component can be deformed to expand outward in the radial direction, so as to make the bladder to expand, so that the surgical tool can be positioned on the body of the patient.

10 Claims, 13 Drawing Sheets

(56) References Cited

U.S. PATENT DOCUMENTS

| | | | | |
|---|---|---|---|---|
| 2007/0078302 | A1* | 4/2007 | Ortiz | A61B 17/3421 600/115 |
| 2008/0058730 | A1* | 3/2008 | Melsheimer | A61B 17/3417 604/177 |
| 2008/0086165 | A1* | 4/2008 | Lyon | A61M 25/0017 606/191 |
| 2013/0035702 | A1* | 2/2013 | Heneveld | A61B 17/0482 606/144 |
| 2014/0316209 | A1* | 10/2014 | Overes | A61B 17/3439 600/206 |

* cited by examiner 20
2
22
221
25
242
241
24
21
1
4
6"
111
6'
10
110

112
112
112b
112a 20
1
4
5
30
33
3
5
302
30
33
21
6"
6
6'

1001
100
1
4
5
301
302
33
10
6"
6
6'

1001
100
1
11
4
31
302
30
5
51
6"
301
33
333
302
6'
301
112b
112
112a
10
110

SURGICAL IMPLEMENT FOR PIERCING TISSUE

TECHNICAL FIELD OF THE INVENTION

The present invention relates to a surgical tool for minimally invasive surgery, for example, endoscopic or laparoscopic surgery, and in particular to a surgical tool for piercing tissue of a body, such as a puncture outfit.

BACKGROUND OF THE INVENTION

Laparoscopic surgery is the most widely used minimally invasive surgery in clinics at present. During surgery, the laparoscopic piercing outfit is used to pierce the human body wall (chest, abdomen, waist, etc.) through the skin, the front end of the sheath of the piercing outfit is left in the abdominal cavity, the thoracic cavity, the posterior abdominal cavity or other body cavities, and the surgical tool is inserted through the passage of the piercing sheath to perform corresponding surgical operations on the tissues and organs in the body cavity. The laparoscopic piercing outfit is a necessary tool in this surgery. The sheaths of the existing laparoscopic piercing outfits have no effective fixation devices after being pierced into the body cavity, so the piercing sheaths often fall out of the body or go deep into the body during the surgical process. If the sheath of the piercing outfit is inserted too deep, there is a risk of damaging organs, the visual field of the endoscope may be blocked, and it is difficult to operate the surgical tool. For example, it is unable to open various forceps, clamps, ultrasonic scalpels or needle holders. Since the sheath of the piercing outfit frequently falls out, the operator has to repeatedly pierce and place the sheath, thereby seriously affecting the progress and quality of the surgery and aggravating the trauma of the patient. In addition, it is necessary to inflate carbon dioxide gas into the human body cavity during the laparoscopic surgery to expand the body cavity, so as to facilitate the operation of the surgical tool. Since there may be a large gap between the sheath of the currently used piercing outfit and the piercing passage of the body wall, it is likely to lead to gas leakage in the cavity. The leakage of a large amount of gas may the collapse of the body cavity without pressure, thereby seriously interfering with the surgical operation. In addition, the leaked gas enters the gaps between subcutaneous loose adipose tissues to form extensive subcutaneous emphysema, thereby increasing the pain of the patient.

At present, the skin suture method is the mostly widely used measure to fix the sheath of the piercing outfit in clinic, that is, a method for fixing the sheath of the piercing outfit by suturing the skin at the pierced part, then passing the line through the preset side hole on the wall of the piercing outfit and knotting the suture line. This fixation method is simple and convenient and can effectively prevent the sheath from falling out, but cannot solve the problems of too deep insertion of the sheath and gas leakage. In view of the current situation where there are no perfect fixation measures for piercing outfits used in the laparoscopic surgery, different researchers have designed various auxiliary fixation structures or devices for piercing outfits, with a fixation function. For example, a Chinese patent CN204428182U (patent NO.: ZL201520070627.4) disclosed a fixation seat for a laparoscopic piercing cannula, wherein the fixation seat comprises an elastic rubber fixation tray that can be sleeved outside a sheath of a piercing outfit. When in use, the tray and the sheath are relatively fixed by using the elastic tightening effect of the rubber material, and the bottom of the tray is fixed to the skin at the piercing position of the human body wall by suturing. Or, similar in-vitro fixation methods are used. For example, a Chinese patent CN203915028U (patent NO.: ZL201420300864.0) disclosed a locating clasp for a laparoscopic piercing outfit, wherein a sheath of a piercing outfit is relatively to a fixation device outside the sheath through a bolt. The design of this in-vitro fixation method can play a role in preventing the sheath of the piercing outfit from being inserted too deep and/or falling out. However, during the actual surgical operation, the sheath of the piercing outfit is repeatedly subjected to the twisting and pushing force, and the sheath and the fixation device sleeved outside the sheath still have a risk of loosening. Moreover, the sleeved fixation device certainly limits the angle of rotation of the sheath of the piercing outfit to a certain extent, thereby interfering the operation of the surgical tool, which is particularly obvious when the tool is operated in a relatively deep and narrow body cavity, such as a posterior abdominal cavity. Therefore, a Chinese patent CN204581447U (patent NO.: ZL201520146655.X) disclosed an anti-off haemostatic piercing outfit for a laparoscope. After the piercing outfit enters the abdominal cavity, a gas or liquid is fed into a gas/liquid feeding pipe through a gas/liquid feeding port to expand the balloon so as to achieve the purpose of fixing the tool. After entering the abdominal cavity, the piercing outfit needs to be filled with a gas or liquid to expand the balloon. However, the arrangement of the gas/liquid feeding port and the gas/liquid feeding pipe on the piercing outfit is likely to make the diameter of the sheath of the piercing outfit larger, and the manufacturing cost and usage cost for the piercing outfit with a balloon are high. Therefore, it is necessary to further improve the existing piercing outfits.

In addition, in clinical practice, balloon piercing outfits are also used in laparoscopic transgastric surgery. In the laparoscopic transgastric surgery, the balloon piercing outfit is directly pierced into the gastric cavity through the abdominal wall. On one hand, the piercing outfits with a gasbag are expensive and inconvenient to popularize. Meanwhile, in order to reserve a gas feeding pipe on the tube wall to feed gas into the gasbag, it is necessary to increase the thickness of the tube wall, so that the diameter of the piercing outfit is increased, and the damage to the abdominal wall and the gastric wall is increased during piercing. In addition, the tube wall cannot be made of a transparent material due to a large thickness, the visual field in the surgery is affected, and surgical risk is increased. Therefore, these piercing outfits are not popularized at present. On the other hand, after a gas is inflated into the gastric cavity, a part of the gas will certainly flow into the intestinal tract, resulting in the bloating of the postoperative patient, which is disadvantageous for the recovery of the intestinal function of the patient. Moreover, after a part of the gas overflows from the oral cavity, the operation space in the gastric cavity will be affected, and it is disadvantageous for the exposure and operation of the lesion. Meanwhile, when the gastric wall is excised through in the process of excising the lump on the gastric wall, the gas in the gastric cavity flows into the abdominal cavity. Thus, the maintenance of the operation in the gastric cavity is affected. More importantly, the gastric juice and the tumor will contaminate the abdominal cavity, which violates the basic principle of sterility and no tumor in the surgery. Therefore, piercing outfits special for gastrocentesis-free inflatable laparoscopic transgastric surgery are obviously necessary.

SUMMARY OF THE INVENTION

It is a first object of the present invention to provide a surgical tool for piercing tissue of a body, which can fix a cannula into which the surgical tool is to be inserted without feeding a gas or liquid.

It is a second object of the present invention to provide a surgical tool for piercing tissue of a body, which can minimize the inhalation of pneumoperitoneum gas to carry out a gastric cavity surgery.

For achieving the first object, the surgical tool for piercing tissue of a body comprises:

- a hollow external component, configured to define a longitudinal axis, having a peripheral wall and a distal end;
- an internal component, at least partially disposed inside the hollow external component, movable inside the external component along the longitudinal axis;
- a plurality of movable components mounted outside the peripheral wall of the external component;
- an actuating portion connected to an outer surface of the internal component, each actuating portion having a slot for receiving a movable pin;
- a plurality of bladders configured to cover the movable components;
- the internal component has a piercing head at the distal end of the external component;
- each movable component has a plurality of movable pins extending into the peripheral wall;
- when the piercing head and the internal component retract relative to the external component, the movable component deforms partially, expands outwardly in a radial direction, and fills the bladder.

In order to better fill the bladders, preferably, the external component has a plurality of limiting holes on the peripheral wall of the external component, for receiving the movable pins and limiting the movement of the movable component; the internal component is capable of rotating relative to the external component while sliding inside the external component, and the movable component is capable of expanding at least partially outward under the action of the rotation of the internal component. When the internal component moves relative to the external component in the longitudinal direction to expose the piercing head (it is defined as the forward direction of the internal component), the internal component can pierce the body wall of the patient; and, when the internal component moves in a backward direction (that is, the internal component moves relative to the external component in a direction away from the distal end of the external component), the socket on the actuating portion of the internal component and the movable pins capable of driving the movable component are deformed to expand outward in the radial direction. The actuation by the deflection force is provided to make the internal component "rotate once" to fill the bladder and make the internal component "rotate once" reversely, so that the internal component is pulled away from the external component, and it is convenient to use the surgical operation inserted into the external component to carry out a surgery.

Preferably, each limiting hole has L-shape, and comprises a first limiting hole portion along the longitudinal axis of the external component and a second limiting hole portion, in communication with the first limiting hole portion, vertical to the longitudinal axis of the external component; when the internal component moves along the longitudinal axis of the external component, each movable pin moves along the first limiting hole portion, and when the internal component rotates relative to the external component, each movable pin moves along the second limiting hole portion. By moving the movable pin of the movable component from the first limiting hole portion to the second limiting hole portion, the internal component is "rotated once" to fill the bladder.

Preferably, each movable component comprises at least two sub-movable components, each sub-movable component having a fixed portion and an expanding portion, a movable ring surrounding the external component and connected to the fixed portions of the sub-movable components; the movable ring is adjacent to the distal end of the external component and the expanding portion is away from the distal end, all sub-movable components in one movable component enclosed forming a ring surrounding the peripheral wall of the external component; the movable pins are connect to an inner surface of each movable ring, and each movable pin has an inclined surface inclining along the circumferential direction of the movable ring. By using the movable ring as a reference, the fixed portion of each sub-movable component is connected to the movable ring, while the free end of each sub-movable component can be deformed to expand outward in the radial direction by using the respective fixed portion as a bearing point; and, the movable pin of each sub-movable component has an inclined surface that deflects in the circumferential direction, and can thus better move into the second limiting hole portion from the first limiting hole portion.

Preferably, a plurality of limiting rings corresponding the plurality of movable components, is disposed on the peripheral wall of the external component, the expanding portions of each movable components is adjacent to the corresponding limiting ring; the expanding portion of each sub-movable component presses against the limiting ring, each limiting ring limits the movement of the expanding portions of the corresponding movable component and forces the expanding portions to expand outward in the radial direction during the rotation of the internal component.

In order to realize the expansion of the bladder, preferably, each limiting ring has a second annular groove away from the distal end of the external component, the movable ring has a third annular groove adjacent to the proximal end of the external component, and two peripheral portions of the bladder are respectively connected in the second annular groove and the third annular groove.

Preferably, the internal component further comprises an operating portion away from the distal end of the external component and allows a surgeon to operate the internal component to move relative to the external component; the peripheral wall of the external component has a mounting hole for mounting the piercing head; the internal component has at least two blocks protruded from the outer surface of the internal component and an annular convex rings located at the tail ends of the blocks adjacent to the mounting hole; and gaps between the adjacent blocks and the annular convex ring form the slot for receiving the movable pin.

Preferably, the blocks has a plurality of first blocks parallel to the longitudinal axis direction of the internal component and a plurality of second blocks extending from the first blocks to the longitudinal axis direction of the internal component; the width of the second blocks extending in the circumferential direction is less than that of the first blocks; a first slot is formed between adjacent first blocks, and a second slot is formed between adjacent second blocks and the annular convex rings; when the internal component moves relative to the external component in a direction away from the distal end of the external component, the movable pin of each sub-movable component enters the first slot of the internal component, and the movable pin of each sub-movable component is capable of entering the second slot of the internal component in a state where the internal component deflects circumferentially by itself, so that the movable pin of the movable component moves into the second limiting hole portion from the first limiting hole portion, and the movable component finally be at least partially deformed to expand outward in the radial direction.

The movable pin of each sub-movable component enters the first slot of the internal component, and the movable pin of each sub-movable component can enter the second slot of the internal component in a state where the internal component deflects circumferentially by itself. When each sub-movable component enters the second slot of the internal component, along with the movement of the internal component relative to the external component in a direction away from the distal end of the external component, the movable pin of each sub-movable component can move along the first limiting hole portion and then "rotate once" the internal component, so that the movable pin of each sub-movable component moves into the second limiting hole portion. Thus, the bladder can be filled, so that the movable component can be at least partially deformed to expand outward in the radial direction. Specifically, when the internal component moves relative to the external component in the longitudinal direction and when the first slot of the internal component slides along the movable pin of each sub-movable component to expose the piercing head, the second slot of the internal component is just aligned with the position of each sub-movable component. When it is necessary to pierce the body wall of the patient, each sub-movable component can fall into the second slot in a state where the internal component deflects circumferentially by itself; and then, when the internal component moves in the backward direction (that is, the internal component moves relative to the external component in a direction away from the distal end of the external component, the movable pin of each sub-movable component can move along the first limiting hole portion and then "rotate once" of the internal component, so that the movable pin of each sub-movable component can move into the second limiting hole portion. Subsequently, the movable component applies a force to the expanding portion of each sub-movable component due to the limitation of the limiting ring, so as to drive each sub-movable component to be deformed to expand outward in the radial direction.

For achieving the second object, preferably, there are two movable components disposed at intervals along the longitudinal axis of the external component, and a plurality of locking ribs capable of engaging with a tissue are disposed at intervals between the adjacent movable components. In order to carry out a gastric cavity surgery, when the piercing head passes through the body wall of the patient to pierce the gastric wall, since there are two movable components, the "once rotation" of the internal component makes the first movable component fill the first bladder, and the external component can be better connected to the gastric wall through the locking ribs. At this time, the internal component "rotates once" reversely, so that the internal component is partially pulled away from the external component and the gastric wall is pulled into the body wall of the patient due to the expansion of the first bladder. At this time, the internal component "rotates once" again to make the second movable component fill the second bladder. At this time, the internal component "rotates once" reversely, so that the internal component is completely pulled away from the external component, and it is convenient to use the surgical tool inserted into the external component to carry out a surgery, avoiding hazards caused by the inflation operation in the gastric cavity.

Preferably, a resisting piece capable of moving relative to the movable components is further disposed on the peripheral wall of the external component, and the resisting piece and the expanded bladders form a clamping space for clamping the abdominal wall of the patient. By providing the resisting piece, the external component can be fixed to the abdominal wall of the patient more stably, thereby preventing the surgical tool for piercing tissue of a body from frequently falling out of the body or going deep into the body during the surgical process.

Compared with the prior art, the present invention has the following advantages. The movable component can be at least partially deformed to expand outward in the radial direction, so as to make the bladder to expand, when the internal component for piercing moves away from the tissue of a body relative to the external component. Thus, a structure similar to the "gasbag or balloon" is formed, so that the purpose of positioning the surgical tool on the body of the patient is achieved, and the operation of feeding a gas or liquid is omitted. And, this surgical tool is easier to use, and the cost for manufacturing and usage is lower.

DETAILED DESCRIPTION OF THE INVENTION

Figure 1:
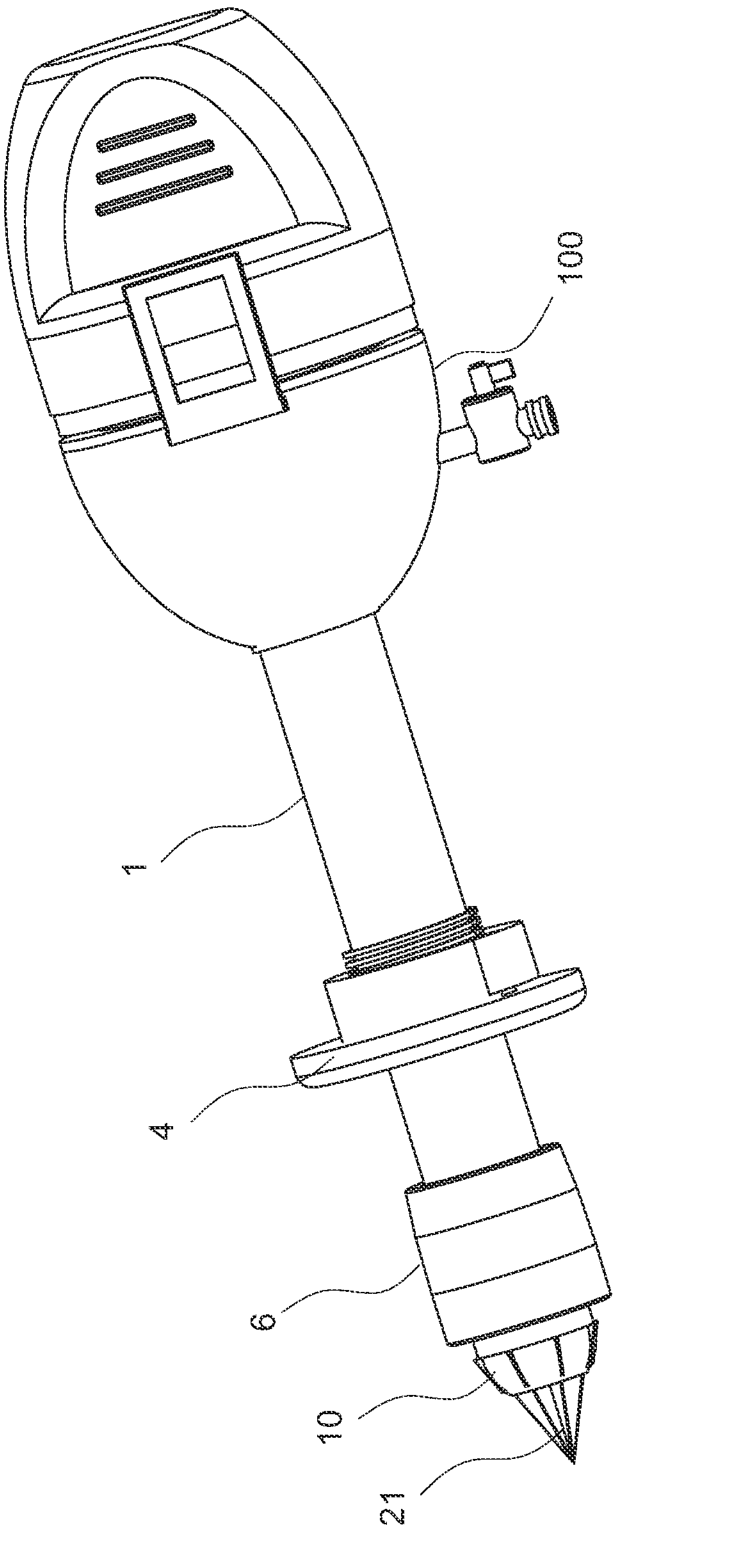
FIG. 1 is a perspective view of a surgical tool for piercing tissue of a body according to an embodiment of the present invention (having a single bladder)
Figure 2:
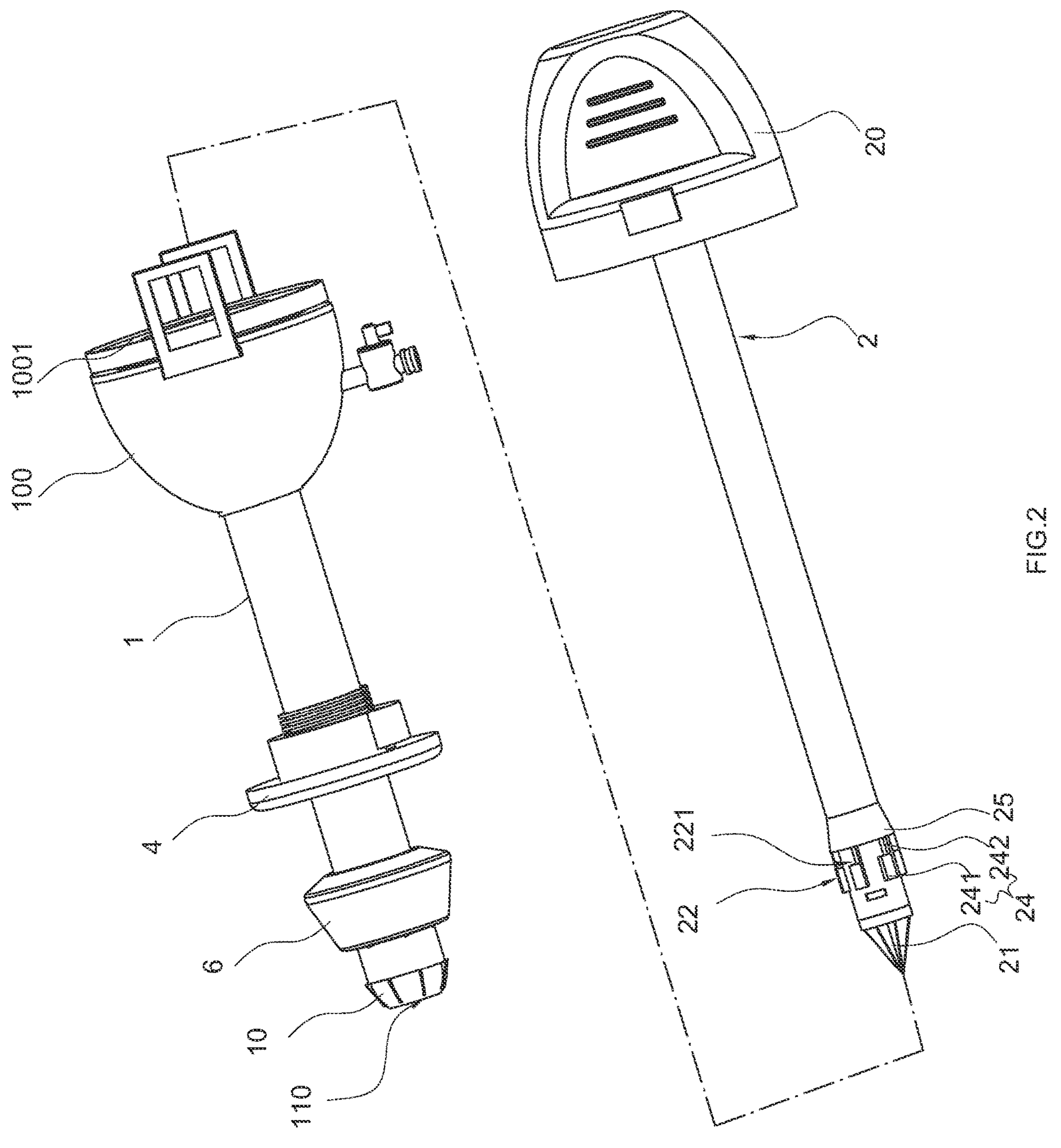
FIG. 2 is an exploded view of FIG. 1.
Figure 3:
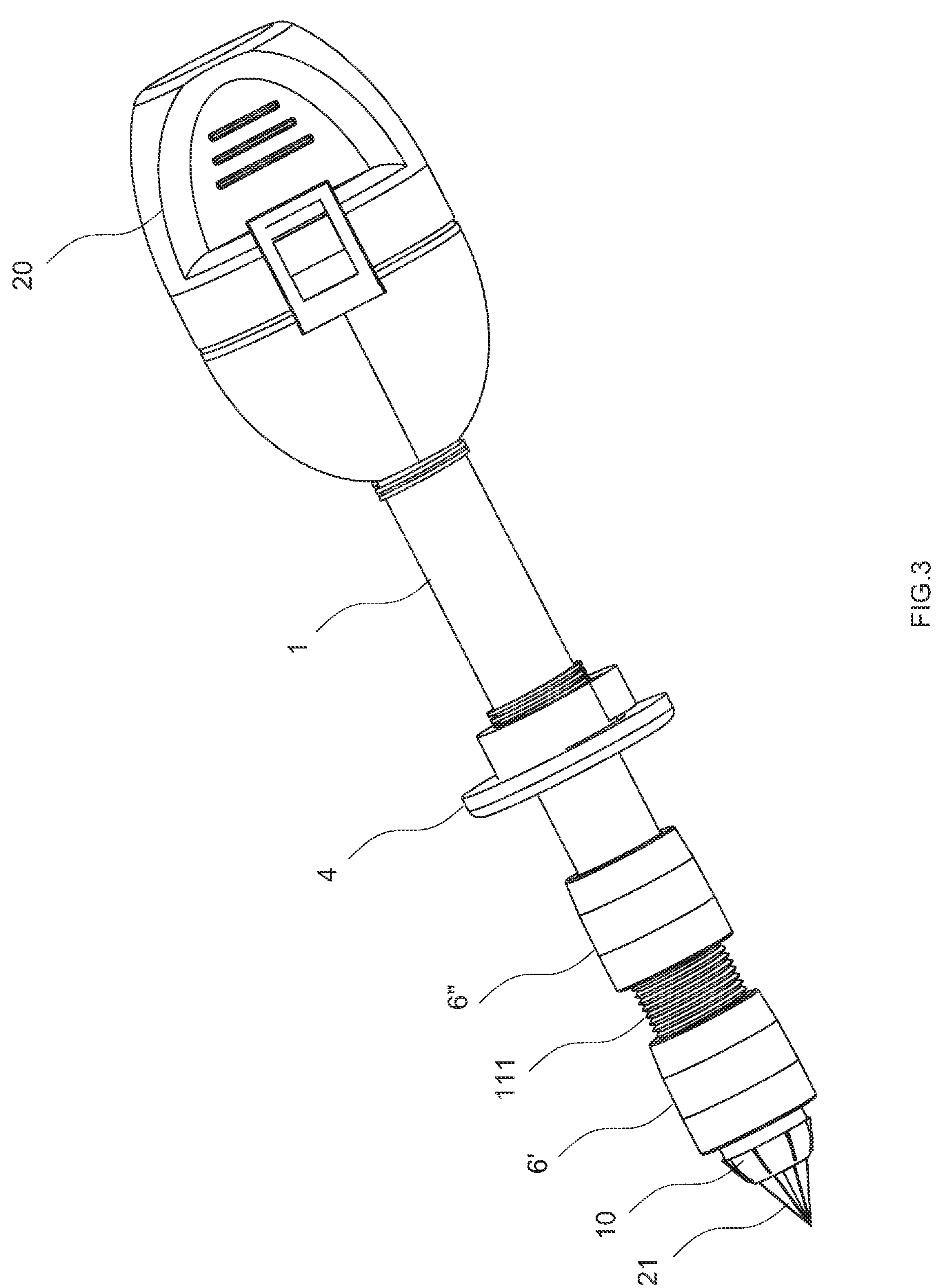
FIG. 3 is a perspective view of the surgical tool for piercing tissue of a body configured to carry out a gastric cavity surgery according to the embodiment of the present invention (having two bladders)
Figure 4:
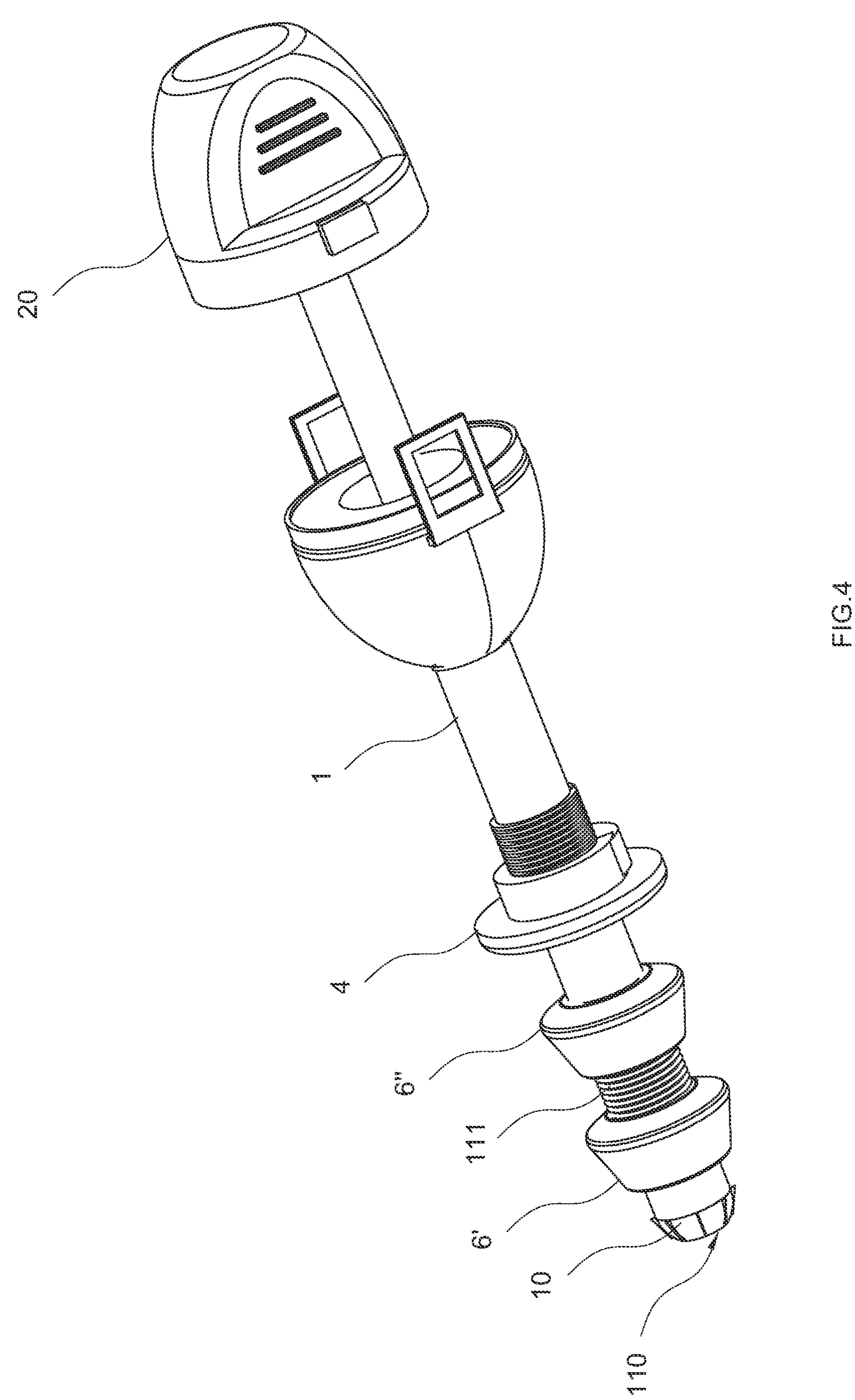
FIG. 4 is a perspective view of a state where a movable component is at least partially deformed to expand outward in the radial direction when an internal component moves relative to an external component in a direction away from a distal end of the external component in FIG. 3.
Figure 5:
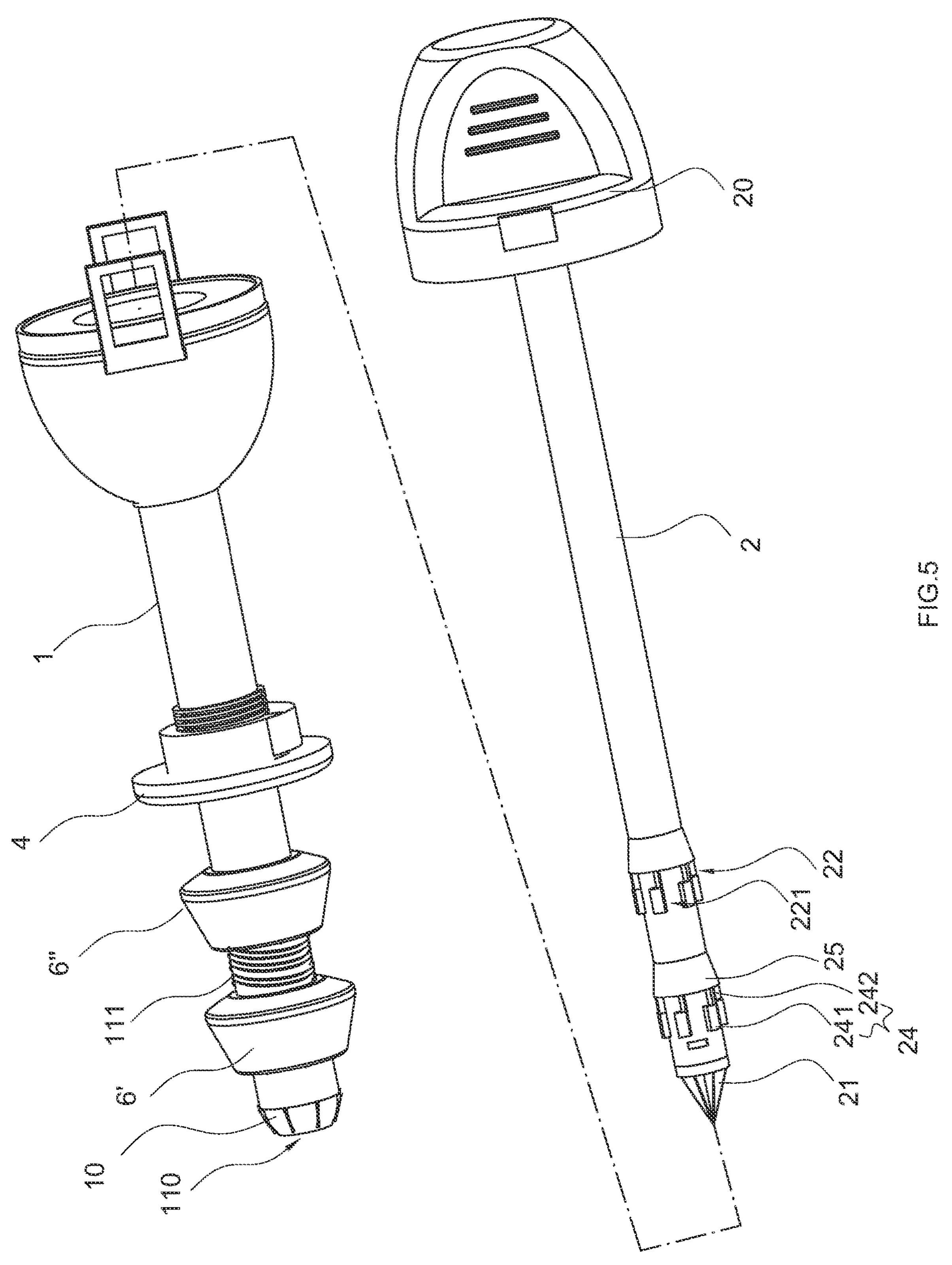
FIG. 5 is an exploded view of FIG. 4.
Figure 6:
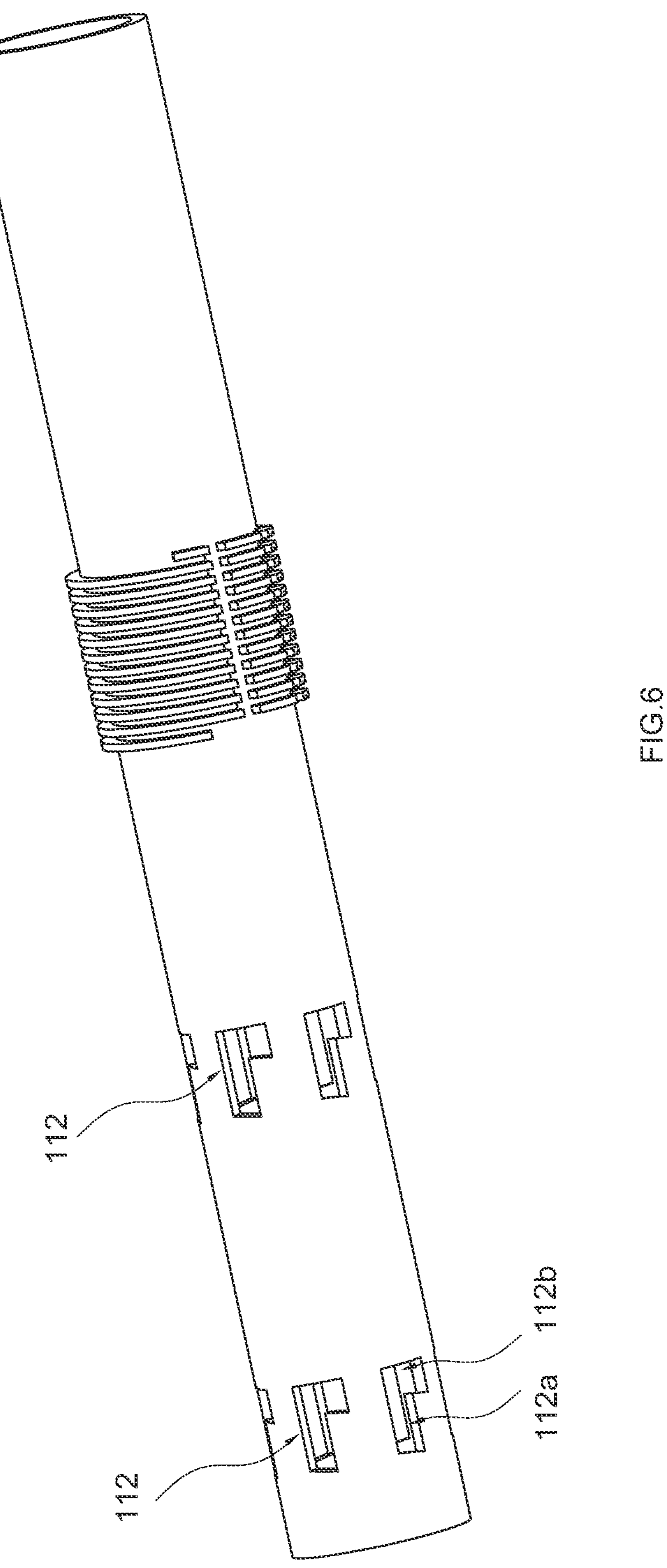
FIG. 6 is a partly perspective view of the external component according to the embodiment of the present invention.
Figure 7:
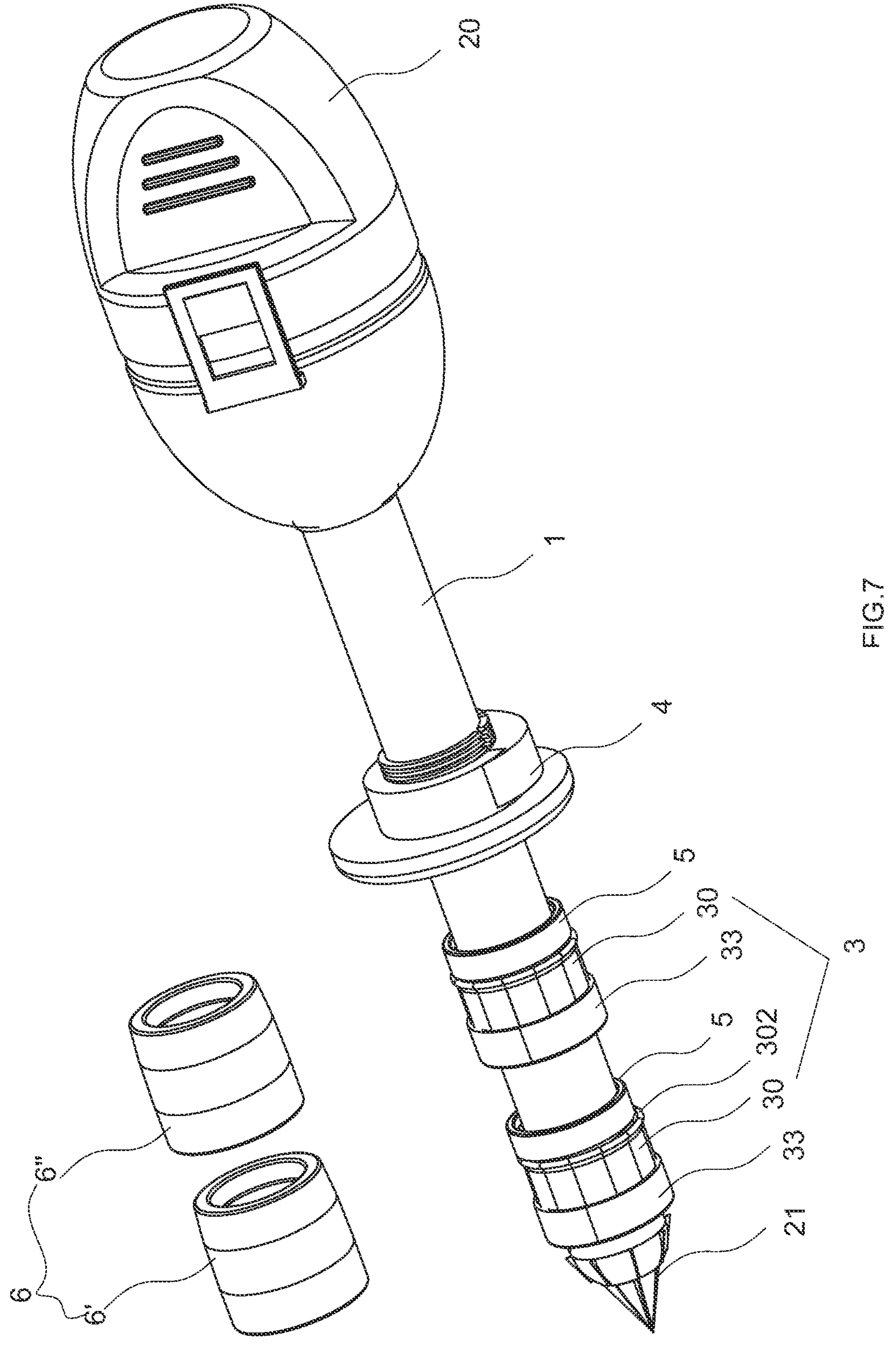
FIG. 7 is an exploded view of FIG. 3.
Figure 8:
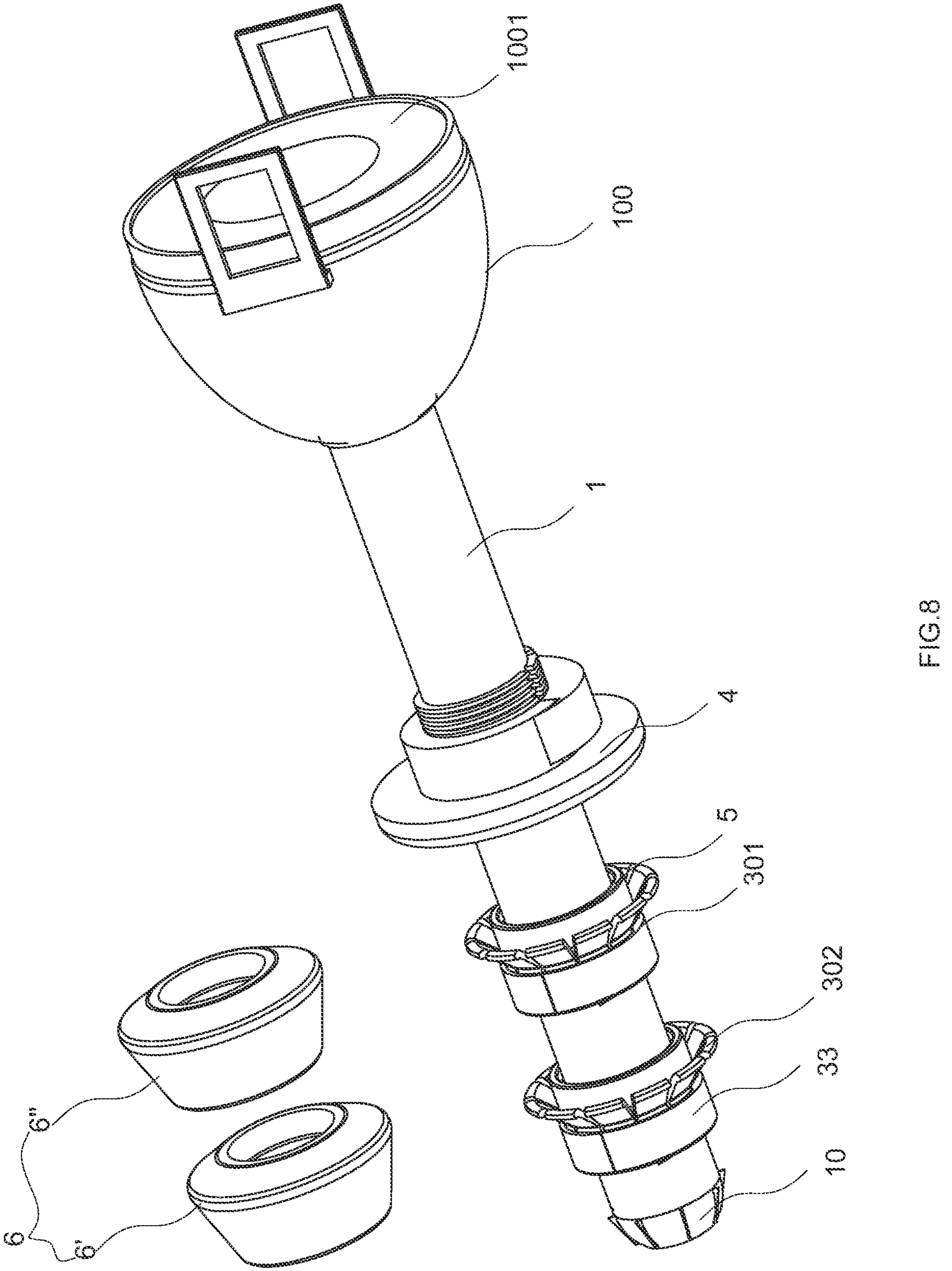
FIG. 8 is a partially exploded view of FIG. 4.
Figure 9:
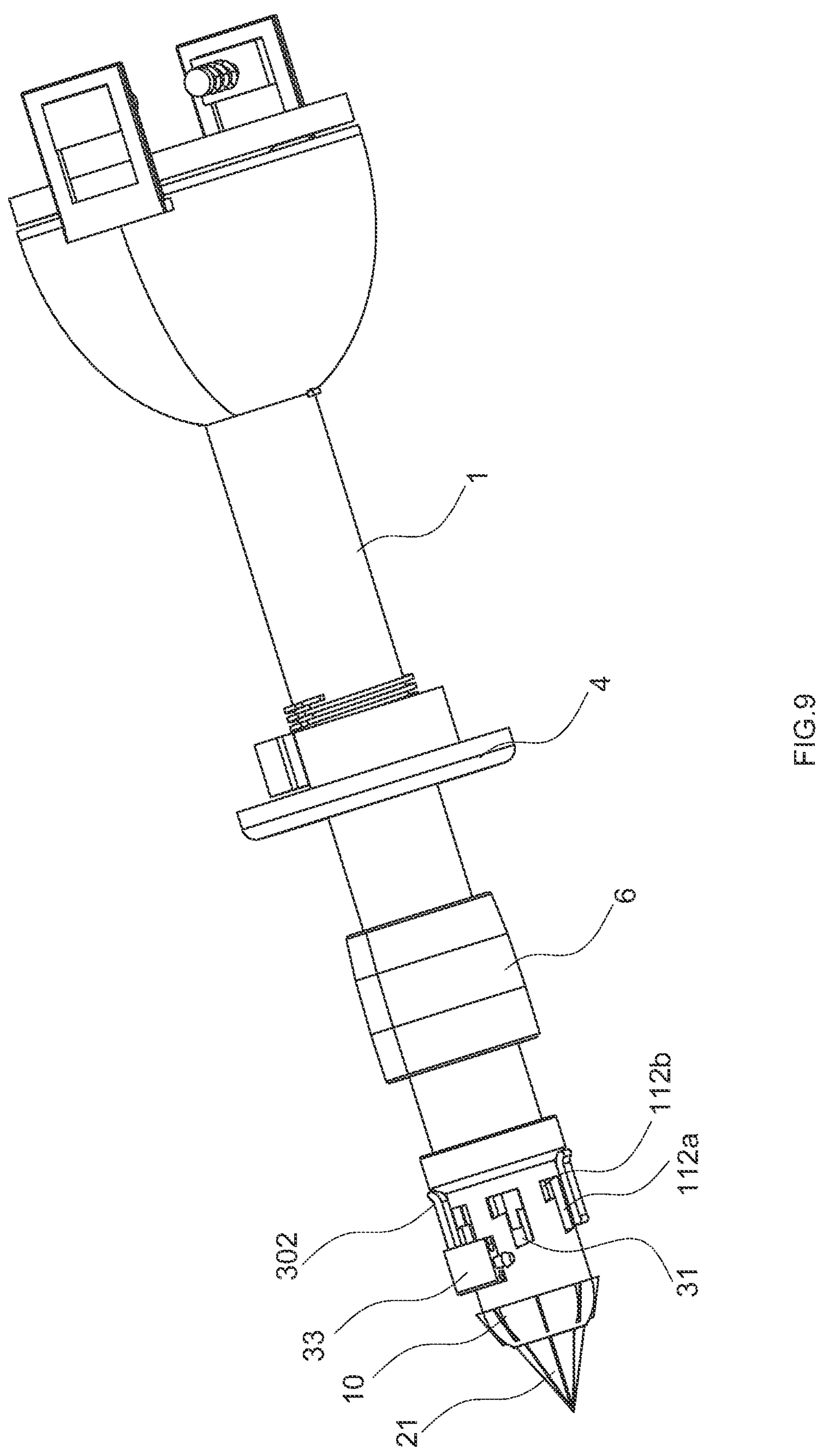
FIG. 9 is a partially exploded view of FIG. 7 (showing that a movable pin of the movable component is located in a first limiting hole portion in a state where a piercing head is at least partially exposed from the outer circumferential wall)
Figure 10:
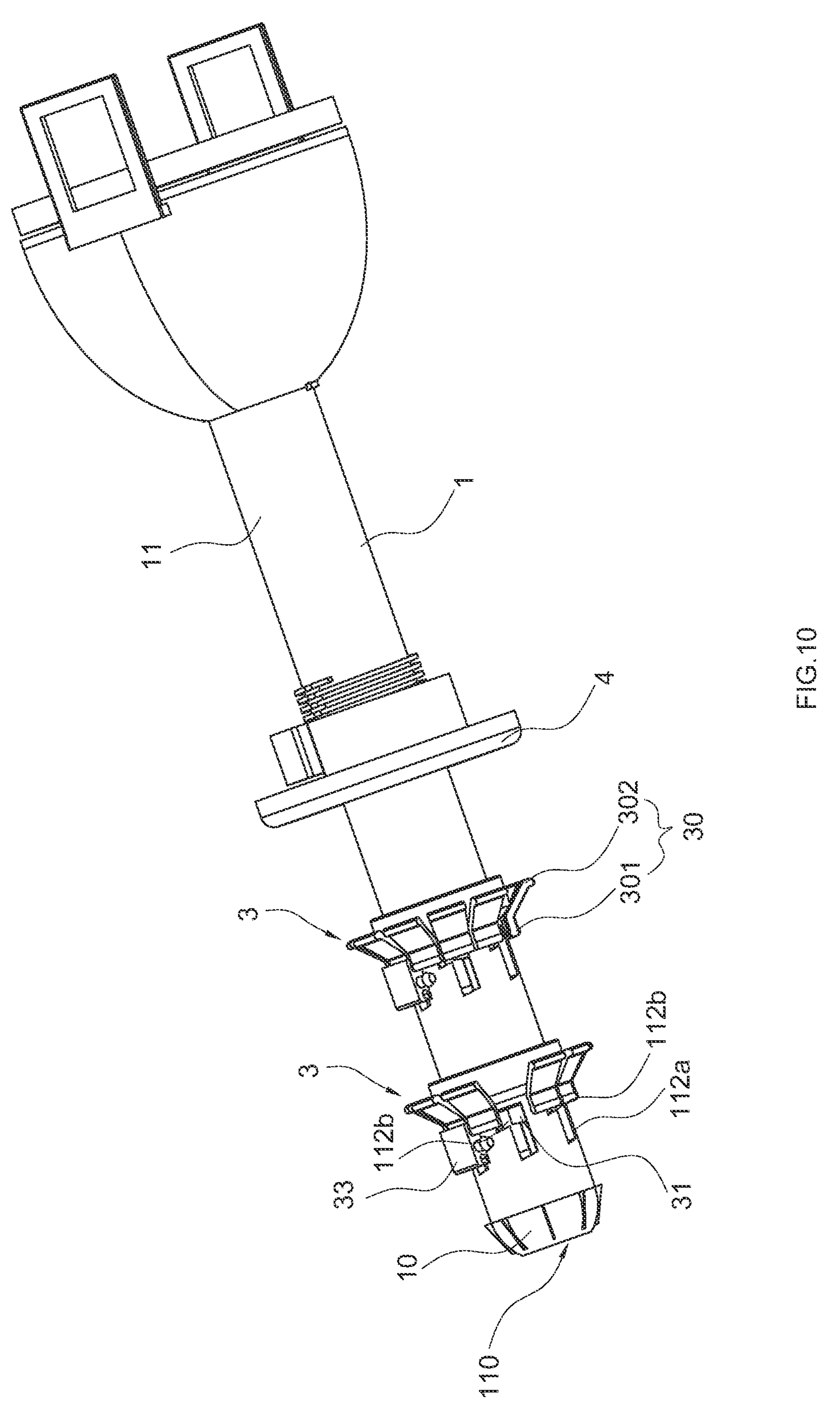
FIG. 10 is a partially exploded view of FIG. 8 (showing that the movable pin of the movable component is located in a second limiting hole portion in a state where the movable component is at least partially deformed to expand outward in the radial direction)
Figure 11:
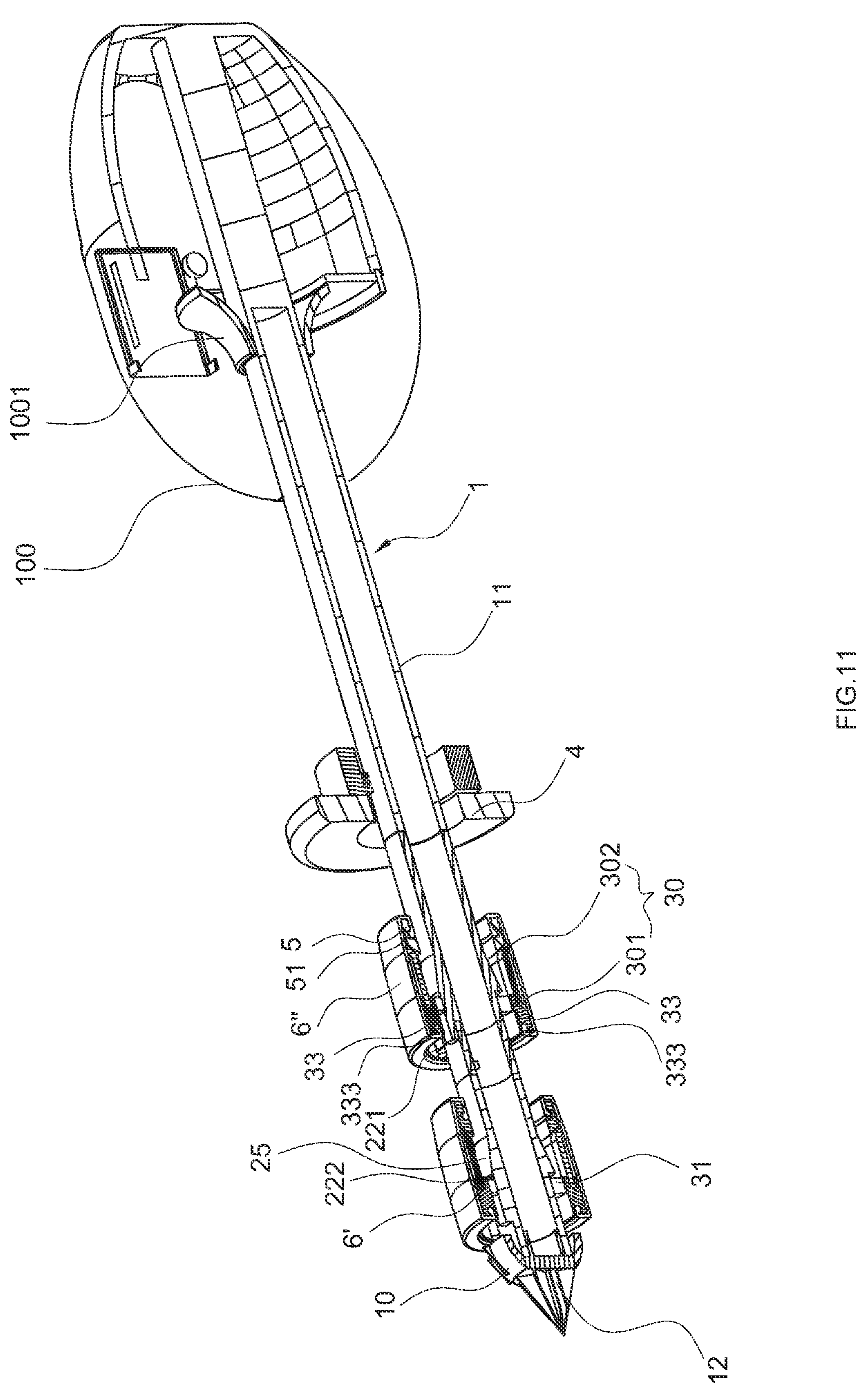
FIG. 11 is a sectional view of FIG. 3.
Figure 12:
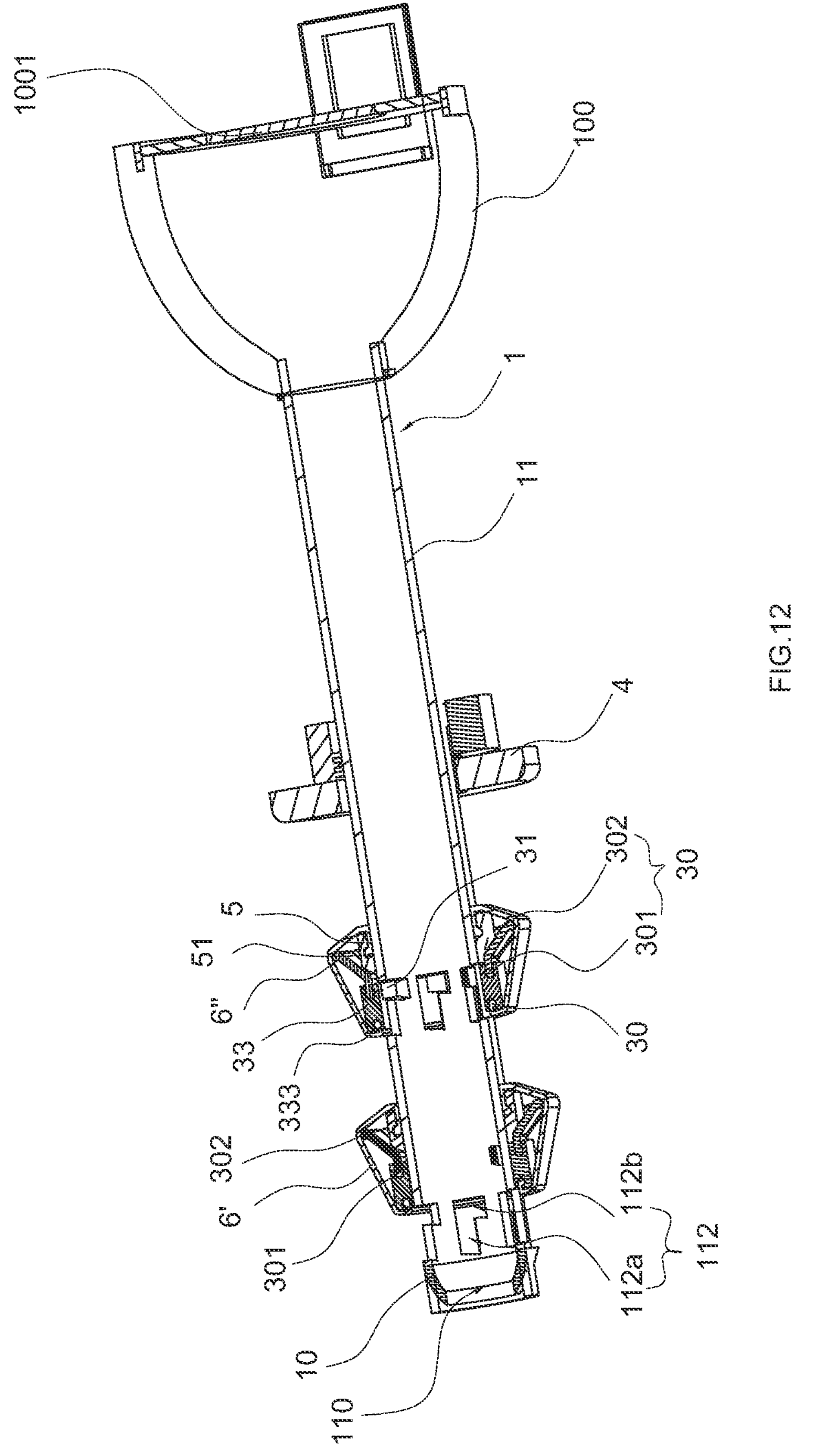
FIG. 12 is a sectional view of FIG. 4.

The present invention will be further described in detail below by embodiments with reference to the accompanying drawings.

FIGS. 1-14 show a preferred embodiment of the present invention. In this embodiment, the surgical tool for piercing tissue of a body comprises a hollow external component 1, an internal component 2, a plurality of movable components 3 disposed on a peripheral wall 11 of the external component 1, and a plurality of bladders 6 for covering the movable component 3.

The external component 1 is configured to define a longitudinal axis and has the peripheral wall 11 and a distal end 10.

The internal component 2 has a piercing head 21 at the distal end 10 of the external component 1 and is at least partially disposed inside the hollow external component 1, movable inside the external component 1 along the longitudinal axis, and can pierce a tissue in a state where the piercing head 21 is at least partially exposed from the peripheral wall 11.

Each movable component 3 has a plurality of movable pins 31 extending into the peripheral wall 11.

An actuating portion 22 is connected to an outer surface of the internal component 2, each actuating portion having a slot 221 for receiving a movable pin 31. When the piercing head 21 and the internal component 2 retract relative to the external component 1, the movable component 3 deforms partially, expands outwardly in a radial direction, and fills the bladder 6.

When the piercing head 21 and the internal component 2 retract relative to the external component 1, the movable component 3 deforms partially, expands outwardly in a radial direction, and fills the bladder 6. Thus, a structure similar to the "gasbag or balloon" is formed, so that the purpose of fixing the surgical tool for piercing tissue of a body to the body wall of the patient is achieved, and the operation of feeding a gas or liquid is omitted. Accordingly, it is easier to use.

Figure 13:
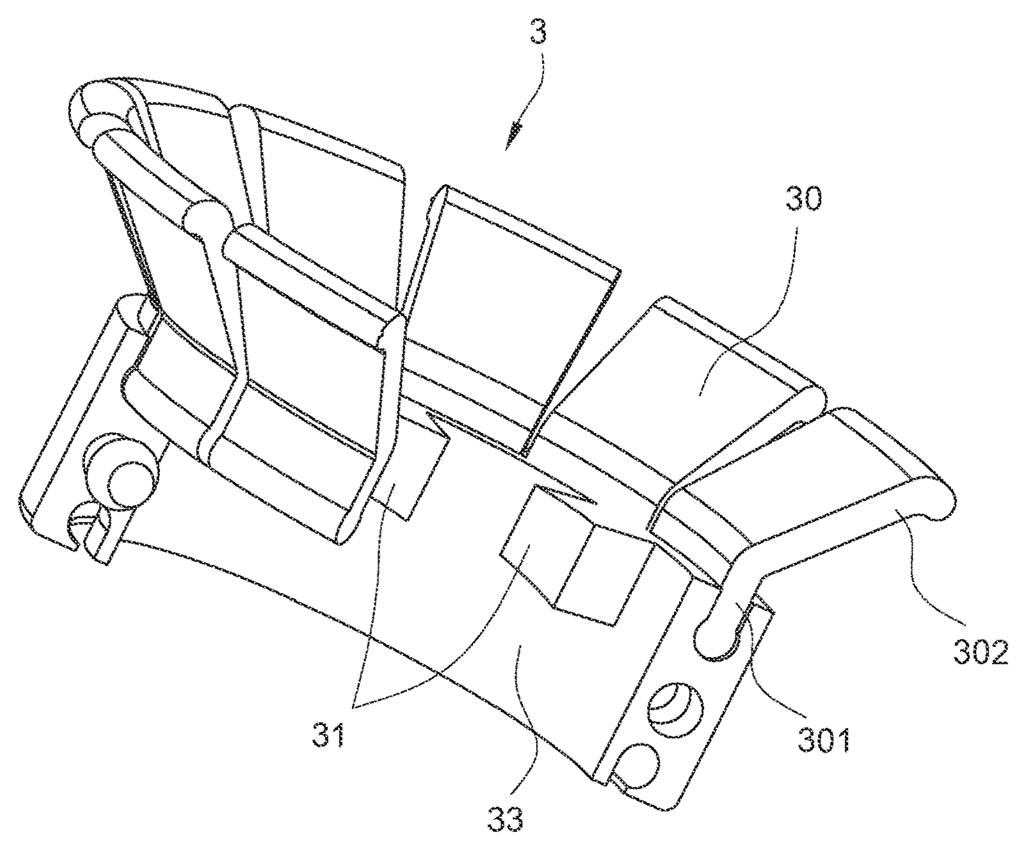
FIG. 13 is a perspective view of part of the movable component according to the embodiment of the present invention.
Figure 14:
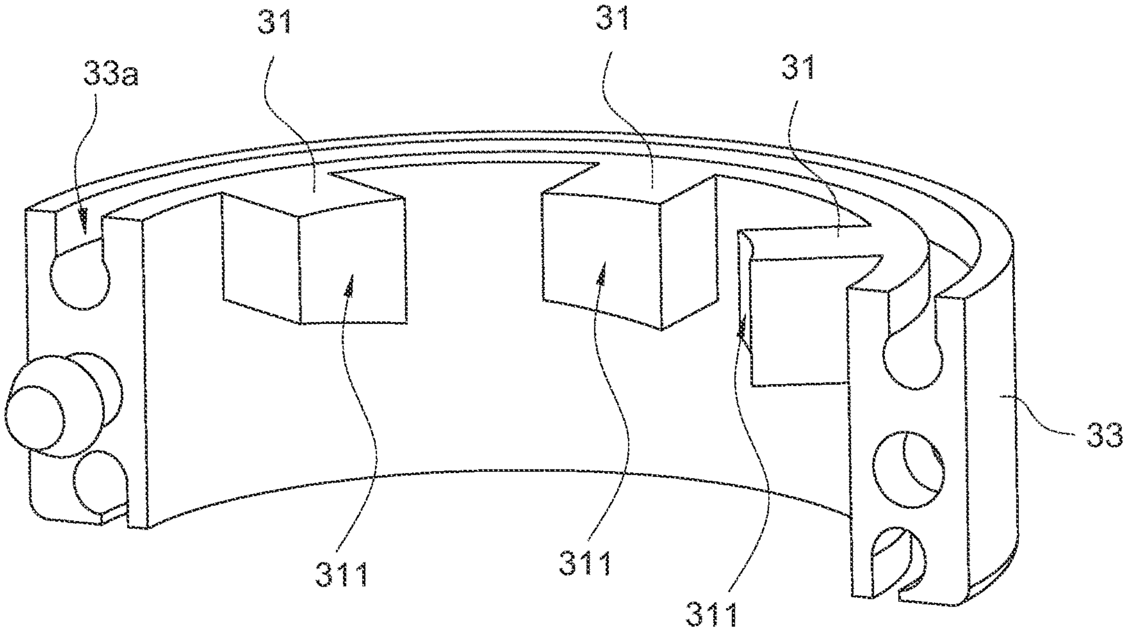
FIG. 14 is a perspective view of the movable ring (one half) according to the embodiment of the present invention.

Specifically, in order to better fill the bladder 6, the external component 1 has a plurality of limiting holes 112 on the peripheral wall 11 of the external component 1, for receiving the movable pins 31 and limiting the movement of the movable component 3; the internal component 2 is capable of rotating relative to the external component 1 while sliding inside the external component 1, and the movable component 3 is capable of expanding at least partially outward under the action of the rotation of the internal component 2. When the internal component 2 rotates relative to the external component 1 in the longitudinal direction to expose the piercing head 21 (it is defined as the forward direction of the internal component 2), the internal component can pierce the body wall of the patient; and then, when the internal component 2 rotates in a backward direction (that is, the internal component 2 rotates relative to the external component 1 in a direction away from the distal end 10 of the external component 1), a slot 221 on the actuating portion 22 of the internal component 2 and the movable pin 3 capable of driving the movable component 3 are deformed to expand outward in the radial direction. The actuation by the deflection force is provided to make the internal component 2 "rotate once" to fill the bladder 6 and make the internal component 2 "rotate once" reversely, so that the internal component 2 is pulled away from the external component 1, and it is convenient to use the surgical operation inserted into the external component 1 to carry out a surgery. Each limiting hole 112 has L-shape, and comprises a first limiting hole portion 112*a* along the longitudinal axis of the external component 1 and a second limiting hole portion 112*b*, in communication with the first limiting hole portion 112*a*, vertical to the longitudinal axis of the external component 1; when the internal component 2 moves along the longitudinal axis of the external component 1, each movable pin 31 moves along the first limiting hole portion 112*a*, and when the internal component 2 rotates relative to the external component 1, each movable pin 31 moves along the second limiting hole portion 112*b*. By moving the movable pin 31 of the movable component 3 from the first limiting hole portion 112*a* to the second limiting hole portion 112*b*, the internal component 2 is "rotated once" to fill the bladder 6. Each movable component 3 comprises at least two sub-movable components 30, each sub-movable component having a fixed portion 301 and an expanding portion 302, a movable ring 33 surrounding the external component 1 and connected to the fixed portions 301 of the sub-movable components 30; the movable ring 33 is adjacent to the distal end 10 of the external component 1 and the expanding portion 302 is away from the distal end 10, all sub-movable components 30 in one movable component 3 enclosed forming a ring surrounding the peripheral wall 11 of the external component 1; the movable pins 31 are connect to an inner surface of each movable ring 33, and each movable pin 31 has an inclined surface 311 inclining along the circumferential direction of the movable ring 33, as shown in FIGS. 13 and 14. By using the movable ring 33 as a reference, the fixed portion 301 of each sub-movable component 30 is connected to the movable ring 33, while the free end of each sub-movable component 30 can be deformed to expand outward in the radial direction by using the respective fixed portion 301 as a bearing point; and, the movable pin 31 of each sub-movable component 30 has an inclined surface 311 that deflects in the circumferential direction and can thus better move into the second limiting hole portion 112*b* from the first limiting hole portion 112*a*. A plurality of limiting rings 5 corresponding the plurality of movable components 3, is disposed on the peripheral wall 11 of the external component 1, the expanding portions 302 of each movable components 3 is adjacent to the corresponding limiting ring 5; the expanding portion 302 of each sub-movable component 30 presses against the limiting ring 5, each limiting ring 5 limits the movement of the expanding portions 302 of the corresponding movable component 3 and forces the expanding portions 302 to expand outward in the radial direction during the rotation of the internal component 2. Each limiting ring 5 has a second annular groove 51 away from the distal end 10 of the external component 1, the movable ring 33 has a third annular groove 333 adjacent to the proximal end of the external component 1, and two peripheral portions of the bladder 6 are respectively connected in the second annular groove 51 and the third annular groove 333. When the expanding portion 302 of each sub-movable component 30 is resisted against the limiting ring 5, each sub-movable component 30 can be driven to be deformed to expand outward in the radial direction. At this time, the movable ring 33 is close to the limiting ring 5, so that the second annular groove 51 is close to the third annular groove 333, and the bladder 6 is thus filled.

In addition, the internal component 2 further comprises an operating portion 20 away from the distal end 10 of the external component 1 and allows a surgeon to operate the internal component 2 to move relative to the external component 1; the peripheral wall 11 of the external component 1 has a mounting hole 110 for mounting the piercing head 21; the internal component 2 has at least two blocks 24 protruded from the outer surface of the internal component 2 and an annular convex rings 25 located at the tail ends of the blocks 24 adjacent to the mounting hole 110; and gaps between the adjacent blocks 24 and the annular convex ring 25 form the slot 221 for receiving the movable pin 31. The blocks 24 has a plurality of first blocks 241 parallel to the longitudinal axis direction of the internal component 2 and a plurality of second blocks 242 extending from the first blocks 241 to the longitudinal axis direction of the internal component 2; the width of the second blocks 242 extending in the circumferential direction is less than that of the first blocks 241; a first slot 221 is formed between adjacent first blocks 241, and a second slot 222 is formed between adjacent second blocks 242 and the annular convex rings 25; when the internal component 2 moves relative to the external component 1 in a direction away from the distal end 10 of the external component 1, the movable pin 31 of each sub-movable component 30 enters the first slot 221 of the internal component 2, and the movable pin 31 of each sub-movable component 30 is capable of entering the second slot 222 of the internal component 2 in a state where the internal component 2 deflects circumferentially by itself, so that the movable pin 31 of the movable component 3 moves into the second limiting hole portion 112*b* from the first limiting hole portion 112*a*, and the movable component 3 finally be at least partially deformed to expand outward in the radial direction. When the internal component 2 moves relative to the external component 1 in the longitudinal direction and when the first slot 221 of the internal component 2 slides along the movable pin 31 of each sub-movable component 30 to expose the piercing head 21, the second slot 222 of the internal component 2 is just aligned with the position of each sub-movable component 30. When it is necessary to pierce the body wall of the patient, each sub-movable component 30 can fall into the second slot 222 in a state where the internal component 2 deflects circumferentially by itself. Then, when the internal component 2 moves in the backward direction (that is, the internal component 2 moves relative to the external component 1 in a direction away from the distal end 10 of the external component 1), the movable pin 31 of each sub-movable component falling into the second slot 222 of the internal component 2 can move into the second limiting hole portion 112*b* from the first limiting hole portion 112*a*. Subsequently, the movable member 3 applies a force to the expanding portion 302 of each sub-movable component 30 due to the limitation of the limiting ring 5, so as to drive each sub-movable component 30 to be deformed to expand outward in the radial direction to realize the expansion of the bladder 6.

In this embodiment, the external component 1 is sleeve-shaped, and a sealing assembly is disposed at the distal end 10 of the external component 1. This sealing assembly is preferably releasably mounted on a sleeve housing 100 located at the distal end 10 of the external component 1. A device for releasably connecting the sealing assembly to the sleeve housing may comprise bayonet coupling, threaded coupling, snap fitting, etc. The sealing assembly comprises a sealing housing and at least one internal sealing piece. The internal sealing piece is suitable for forming a fluid sealing membrane 1001 or a valve body around a tool that is inserted through the sealing assembly. The sealing assembly may be or may not be a component of the sleeve assembly, and the valve structure is closed in the absence of the surgical tool and suitable for preventing pneumoperitoneum gas from passing through the external component 1. In this embodiment, the sealing assembly is a sealing membrane 1001, and the piercing head 21 is a pointed or truncated conical structure. During a gastric cavity surgery, when the internal component 2 moves relative to the external component 1 in the longitudinal direction and when the first slot 221 of the internal component 2 slides along the movable pin 31 of each sub-movable component 30 to expose the piercing head 21, the second slot 222 of the internal component 2 is just aligned with the position of each sub-movable component 30. When it is necessary to puncture the body wall of the patient, each sub-movable component 30 can fall into the second slot 222 in a state where the internal component 2 deflects circumferentially by itself. Then, when the internal component 2 moves in the backward direction (that is, the internal component 2 moves relative to the external component 1 in a direction away from the distal end 10 of the external component 1), the movable pin 31 of each sub-movable component falling into the second slot 222 of the internal component 2 can move into the second limiting hole portion 112*b* from the first limiting hole portion 112*a*. Subsequently, the movable member 3 applies a force to the expanding portion 302 of each sub-movable component 30 due to the limitation of the limiting ring 5, so as to drive each sub-movable component 30 to be deformed to expand outward in the radial direction to realize the expansion of the bladder 6. Then, a resisting piece 4 on the peripheral wall 11 of the external component 1 is moved to the abdominal wall of the patient, and the resisting piece 4 and the expanded bladder 6 form a clamping space for clamping, thereby preventing the surgical tool for piercing tissue of a body from frequently falling out of the body or going deep into the body during the surgical process.

Finally, the surgical tool for piercing tissue of a body in this embodiment can be used to carry out a gastric cavity surgery (referring to FIGS. 3-12). During the gastric cavity surgery, there are two movable components 3 disposed at intervals along the longitudinal axis of the external component 1, and a plurality of locking ribs 111 capable of engaging with a tissue are disposed at intervals between the adjacent movable components 3. In order to carry out a gastric cavity surgery, when the piercing head 21 passes through the body wall of the patient to pierce the gastric wall, since there are two movable components 3, the "once rotation" of the internal component 2 makes the first movable component 3' expand the first bladder 6', and the external component 1 can be better connected to the gastric wall through the locking ribs 111. At this time, the internal component 2 "rotates once" reversely, so that the internal component 2 is partially pulled away from the external component 1, and the gastric wall is pulled into the body wall of the patient due to the expansion of the first bladder 6'. At this time, the internal component 2 "rotates once" again to make the second movable component 3" expands the second bladder 6". At this time, the internal component 2 "rotates once" reversely, so that the internal component 2 is completely pulled away from the external component 1, and it is convenient to use the surgical tool inserted into the external component 1 to carry out a surgery, avoiding hazards caused by the inflation operation in the gastric cavity. A resisting piece 4 capable of moving relative to the movable components 3 is further disposed on the peripheral wall 11 of the external component 1, and the resisting piece 4 and the expanded bladders 6 form a clamping space for clamping the abdominal wall of the patient. Finally, by providing the resisting piece 4, the external component 1 can be fixed to the abdominal wall of the patient more stably, thereby preventing the surgical tool for piercing tissue of a body from frequently falling out of the body or going deep into the body during the surgical process. After the surgery is finished, the first bladder 6' and the second bladder 6" need to be folded by means of the internal component 2. The specific operation is opposite to the operating unfolding the first bladder 6' and the second bladder 6".

The invention claimed is:

1. A surgical tool for piercing tissue of a body, comprising:

a hollow external component (1), configured to define a longitudinal axis, having a peripheral wall (11) and a distal end (10);

an internal component (2), at least partially disposed inside the hollow external component (1), movable inside the external component (1) along the longitudinal axis;

a plurality of movable components (3) mounted outside the peripheral wall (11) of the external component (1);

an actuating portion (22) connected to an outer surface of the internal component (2), each actuating portion having a slot (221) for receiving a movable pin (31);

a plurality of bladders (6) configured to cover the movable components (3);

wherein, the internal component (2) has a piercing head (21) at the distal end (10) of the external component (1);

each movable component (3) has a plurality of movable pins (31) extending into the peripheral wall (11);

when the piercing head (21) and the internal component (2) retract relative to the external component (1), each movable component (3) deforms partially, expands outwardly in a radial direction, and fills a corresponding bladder (6).

2. The surgical tool of claim 1, wherein the external component (1) has a plurality of limiting holes (112) on the peripheral wall (11) of the external component (1), for receiving the movable pins (31) and limiting the movement of the movable component (3);

the internal component (2) is capable of rotating relative to the external component (1) while sliding inside the external component (1), and each movable component (3) is capable of expanding at least partially outward under the action of the rotation of the internal component (2).

3. The surgical tool of claim 2, wherein each limiting hole (112) has L-shape, and comprises a first limiting hole portion (112*a*) along the longitudinal axis of the external component (1) and a second limiting hole portion (112*b*), in communication with the first limiting hole portion (112*a*), vertical to the longitudinal axis of the external component (1);

when the internal component (2) moves along the longitudinal axis of the external component (1), each movable pin (31) moves along the first limiting hole portion (112*a*), and when the internal component (2) rotates relative to the external component (1), each movable pin (31) moves along the second limiting hole portion (112*b*).

4. The surgical tool of claim 3, wherein each movable component (3) comprises at least two sub-movable components (30), each sub-movable component having a fixed portion (301) and an expanding portion (302), a movable ring (33) surrounding the external component (1) and connected to the fixed portions (301) of the sub-movable components (30);

the movable ring (33) is adjacent to the distal end (10) of the external component (1) and the expanding portion (302) is away from the distal end (10), all sub-movable components (30) in one movable component (3) enclosed forming a ring surrounding the peripheral wall (11) of the external component (1);

the movable pins (31) are connected to an inner surface of each movable ring (33), and each movable pin has an inclined surface (311) inclining along the circumferential direction of the movable ring (33).

5. The surgical tool of claim 4, wherein a plurality of limiting rings (5) corresponding to the plurality of movable components (3), is disposed on the peripheral wall (11) of the external component (1), the expanding portions (302) of each movable component (3) is adjacent to the corresponding limiting ring (5);

the expanding portion (302) of each sub-movable component (30) presses against the limiting ring (5), each limiting ring (5) limits the movement of the expanding portions (302) of the corresponding movable component (3) and forces the expanding portions (302) to expand outward in the radial direction during the rotation of the internal component (2).

6. The surgical tool of claim 5, wherein each limiting ring (5) has a second annular groove (51) away from the distal end (10) of the external component (1), the movable ring (33) has a third annular groove (333) adjacent to the proximal end of the external component (1), and two peripheral portions of the bladder (6) are respectively connected in the second annular groove (51) and the third annular groove (333).

7. The surgical tool of claim 3, wherein the internal component (2) further comprises an operating portion (20) away from the distal end (10) of the external component (1) and allows a surgeon to operate the internal component (2) to move relative to the external component (1);

the peripheral wall (11) of the external component (1) has a mounting hole (110) for mounting the piercing head (21);

the internal component (2) has at least two blocks (24) protruding from the outer surface of the internal component (2), and annular convex rings (25) located at the tail ends of the blocks (24) adjacent to the mounting hole (110); and gaps between the adjacent blocks (24) and the corresponding annular convex ring (25) form the slot (221) for receiving the movable pin (31).

8. The surgical took of claim 7, wherein the blocks (24) have a plurality of first blocks (241) parallel to the longitudinal axis direction of the internal component (2) and a plurality of second blocks (242) extending from the first blocks (241) to the longitudinal axis direction of the internal component (2);

the width of the second blocks (242) extending in the circumferential direction is less than that of the first blocks (241);

a first slot (221) is formed between adjacent first blocks (241), and a second slot (222) is formed between adjacent second blocks (242) and the annular convex rings (25);

when the internal component (2) moves relative to the external component (1) in a direction away from the distal end (10) of the external component (1), the movable pin (31) of each sub-movable component (30) enters the first slot (221) of the internal component (2), and the movable pin (31) of each sub-movable component (30) is capable of entering the second slot (222)

of the internal component (2) in a state where the internal component (2) deflects circumferentially by itself, so that the movable pin (31) of the movable component (3) moves into the second limiting hole portion (**112*b*) from the first limiting hole portion (112*a*), and the movable component (3**) finally be at least partially deformed to expand outward in the radial direction.

9. The surgical tool of claim 8, wherein there are two movable components (3) disposed at intervals along the longitudinal axis of the external component (1), and a plurality of locking ribs (111) capable of engaging with a tissue are disposed at intervals between the adjacent movable components (3).

10. The surgical tool of claim 8, further comprising a resisting piece (4) capable of moving relative to each of the movable components (3) and disposed on the peripheral wall of the external component (1), and the resisting piece (4) and the expanded bladders (6) form a clamping space for clamping the abdominal wall of the patient.

* * * * *